(12) United States Patent
Flynn et al.

(10) Patent No.: US 8,071,816 B2
(45) Date of Patent: Dec. 6, 2011

(54) HYDROFLUOROACETAL COMPOUNDS AND PROCESSES FOR THEIR PREPARATION AND USE

(75) Inventors: Richard M. Flynn, Mahtomedi, MN (US); Michael G. Costello, Afton, MN (US)

(73) Assignee: 3M Innovative Properties Company, Saint Paul, MN (US)

(*) Notice: Subject to any disclaimer, the term of this patent is extended or adjusted under 35 U.S.C. 154(b) by 447 days.

(21) Appl. No.: 12/164,369

(22) Filed: Jun. 30, 2008

(65) Prior Publication Data

US 2009/0326083 A1 Dec. 31, 2009

(51) Int. Cl.
C07C 43/00 (2006.01)

(52) U.S. Cl. ........ 568/677; 165/80.4; 165/80.5; 216/52; 252/2; 252/67; 252/68; 252/70; 427/445; 510/108; 510/506; 521/82; 521/99; 568/413; 568/416; 568/682; 568/683

(58) Field of Classification Search .................. 568/677, 568/683, 413, 416, 682; 570/124, 134, 142; 252/2, 67, 68, 70; 510/108, 506; 216/52; 521/82, 99; 165/80.4, 80.5; 427/445
See application file for complete search history.

(56) References Cited

U.S. PATENT DOCUMENTS

| | | | |
|---|---|---|---|
| 3,903,012 A | 9/1975 | Brandreth | |
| 4,169,807 A | 10/1979 | Zuber | |
| 5,104,034 A | 4/1992 | Hansen et al. | |
| 5,120,459 A * | 6/1992 | Kalota et al. | 508/582 |
| 5,125,089 A | 6/1992 | McCambridge | |
| 5,125,978 A | 6/1992 | Flynn et al. | |
| 5,182,342 A | 1/1993 | Feiring et al. | |
| 5,210,106 A | 5/1993 | Dams et al. | |
| 5,539,008 A | 7/1996 | Dams et al. | |
| 5,543,567 A * | 8/1996 | Bierschenk et al. | 562/582 |
| 5,563,235 A | 10/1996 | Farnham | |
| 5,718,293 A | 2/1998 | Flynn et al. | |
| 5,925,611 A | 7/1999 | Flynn et al. | |
| 5,994,599 A * | 11/1999 | Petrov | 570/136 |
| 6,080,448 A | 6/2000 | Leiner et al. | |
| 6,204,299 B1 * | 3/2001 | Moore et al. | 521/114 |
| RE37,119 E | 4/2001 | Sherwood | |
| 6,303,080 B1 * | 10/2001 | Tuma | 422/38 |
| 6,372,700 B1 * | 4/2002 | Zazerra et al. | 510/175 |
| 6,374,907 B1 | 4/2002 | Tousignant et al. | |
| 6,399,729 B1 | 6/2002 | Farnham et al. | |
| 6,759,374 B2 | 7/2004 | Milbrath et al. | |
| 2005/0127322 A1 | 6/2005 | Costello et al. | |
| 2005/0171388 A1 * | 8/2005 | Tortelli et al. | 568/677 |
| 2005/0197408 A1 * | 9/2005 | Shirakawa et al. | 514/723 |
| 2007/0051916 A1 | 3/2007 | Flynn et al. | |

FOREIGN PATENT DOCUMENTS

| JP | 2001048821 | 2/2001 |
|---|---|---|
| WO | WO 2007/030314 A2 | 3/2007 |

OTHER PUBLICATIONS

PCT International Search Report, PCT/US2009/045775, 3 pages.
Research Disclosure, 40576, Rydroftuoroethers as Fluoromonomer Reaction Media, pp. 81-82 (Jan. 1998).
Tetrahedron Letters, 41, pp. 5873-5876 (2000).
Journal of Fiuorine Chemistry, 61, pp. 217-222 (1993).

* cited by examiner

Primary Examiner — John Cooney
(74) Attorney, Agent, or Firm — Philip Y. Dahl

(57) ABSTRACT

The present disclosure provides a compound according to the formula:

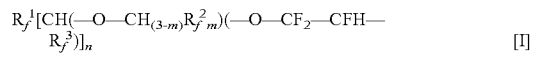

[I]

wherein n is 1 or 2, wherein m is 1, 2 or 3, wherein, when n is 1, $R_f^1$ is selected from the group consisting of highly fluorinated alkyl groups which are linear, branched, cyclic, or a combination thereof, which may optionally be substituted, and which may optionally contain one or more catenated heteroatoms; wherein, when n is 2, $R_f^1$ is selected from the group consisting of highly fluorinated alkylene groups which are linear, branched, cyclic, or a combination thereof, which may optionally be substituted, and which may optionally contain one or more catenated heteroatoms; wherein each $R_f^2$ is independently selected from the group consisting of alkyl groups which are linear, branched, cyclic, or a combination thereof, which may optionally be substituted, and which may optionally contain one or more catenated heteroatoms; wherein at least one $R_f^2$ is highly fluorinated; wherein each $R_f^3$ is independently selected from the group consisting of fluorine and highly fluorinated alkyl groups which are linear, branched, cyclic, or a combination thereof, which may optionally be substituted, and which may optionally contain one or more catenated heteroatoms. Also provided are methods of use and manufacture of such compounds.

45 Claims, No Drawings

HYDROFLUOROACETAL COMPOUNDS AND PROCESSES FOR THEIR PREPARATION AND USE

FIELD OF THE DISCLOSURE

This disclosure relates to a novel class of hydrofluoroacetal compounds and novel processes for their preparation and use.

SUMMARY OF THE DISCLOSURE

Briefly, the present disclosure provides a compound according to the formula:

$$R_f^1[CH(\!-\!O\!-\!CH_{(3-m)}R_f^2{}_m)(\!-\!O\!-\!CF_2\!-\!CFH\!-\!R_f^3)]_n \quad [I]$$

wherein n is 1 or 2, wherein m is 1, 2 or 3, wherein, when n is 1, $R_f^1$ is selected from the group consisting of highly fluorinated alkyl groups which are linear, branched, cyclic, or a combination thereof, which may optionally be substituted, and which may optionally contain one or more catenated heteroatoms; wherein, when n is 2, $R_f^1$ is selected from the group consisting of highly fluorinated alkylene groups which are linear, branched, cyclic, or a combination thereof, which may optionally be substituted, and which may optionally contain one or more catenated heteroatoms; wherein each $R_f^2$ is independently selected from the group consisting of alkyl groups which are linear, branched, cyclic, or a combination thereof, which may optionally be substituted, and which may optionally contain one or more catenated heteroatoms; wherein at least one $R_f^2$ is highly fluorinated; wherein each $R_f^3$ is independently selected from the group consisting of fluorine and highly fluorinated alkyl groups which are linear, branched, cyclic, or a combination thereof, which may optionally be substituted, and which may optionally contain one or more catenated heteroatoms. In some embodiments, some or all of $R_f^1$, $R_f^2$ and $R_f^3$ are perfluorinated. In some embodiments, each $R_f^1$, $R_f^2$ and $R_f^3$ is independently chosen from the group consisting of perfluorinated and nearly perfluorinated C1-C4 alkyl groups which may optionally contain one or more catenated oxygen atoms, typically perfluoromethyl or perfluoroethyl.

In some embodiments, the compound may have a specific enantiomeric form, typically at each carbon marked with an asterisk in formula I':

$$R_f^1[C^*H(\!-\!O\!-\!CH_{(3-m)}R_f^2{}_m)(\!-\!O\!-\!CF_2\!-\!C^*FH\!-\!R_f^3)]_n \quad [I]$$

In another aspect, the present disclosure provides a method of making a compound, including the compound described above, comprising the step of:

a) reacting a compound according to the formula:

$$R_f^1[CH(\!-\!O\!-\!CH_{(3-m)}R_f^2{}_m)(\!-\!OH)]_n \quad [II]$$

with one or more compounds according to the formula:

$$CF_2\!=\!CF\!-\!R_f^3 \quad [III]$$

to form the compound according to the formula:

$$R_f^1[CH(\!-\!O\!-\!CH_{(3-m)}R_f^2{}_m)(\!-\!O\!-\!CF_2\!-\!CFH\!-\!R_f^3)]_n \quad [I]$$

wherein n, m, $R_f^1$, $R_f^2$ and $R_f^3$ are as defined above. In some embodiments, the reaction is performed in the presence of a catalyst, typically potassium carbonate. In some embodiments, the method additionally comprises the step of:

b) reacting a compound according to the formula:

$$R_f^1[CHO]_n \quad [V]$$

with one or more compounds according to the formula:

$$HO\!-\!CH_{(3-m)}R_f^2{}_m \quad [VI]$$

to form the compound according to the formula:

$$R_f^1[CH(\!-\!O\!-\!CH_{(3-m)}R_f^2{}_m)(\!-\!OH)]_n \quad [II]$$

wherein n, m, $R_f^1$ and $R_f^2$ are as defined above. In some embodiments, the method additionally comprises the step of:

c) reacting a compound according to the formula:

$$R_f^1[CH(OR)OH]_n \quad [IV]$$

with one or more dehydrating agents to form the compound according to the formula:

$$R_f^1[CHO]_n \quad [V]$$

wherein n and $R_f^1$ are as defined above and R is selected from the group consisting of alkyl groups which are linear, branched, cyclic, or a combination thereof, which may optionally be substituted, and which may optionally contain one or more catenated heteroatoms. Typically, the one or more dehydrating agents comprises sulfuric acid. In some embodiments, step c) is performed in a first reaction chamber and the compound according to formula V formed therein is distilled from the first reaction chamber upon formation into a second reaction chamber wherein step b) is performed.

In another aspect, the present disclosure provides methods of using compounds, including the compound described above, to remove a contaminant; to extinguish fires; as a blowing agent in the manufacture of foamed plastics; to carry out vapor phase soldering; as a heat transfer agent; as a coating solvent; as a working fluid for cutting or abrasion; or as a polymerization monomer.

As used in this patent application:

"catenated heteroatom" means an atom other than carbon (for example, oxygen, nitrogen, or sulfur) that is bonded to carbon atoms in a carbon chain so as to form a carbon-heteroatom-carbon chain;

"highly fluorinated" means containing fluorine in an amount of 40 wt % or more, more typically 45 wt % or more, more typically 50 wt % or more and most typically 60 wt % or more;

"perfluoro-" (for example, in reference to a group or moiety, such as in the case of "perfluoroalkylene" or "perfluoroalkyl" or "perfluorocarbon") or "perfluorinated" means completely fluorinated such that there are no carbon-bonded hydrogen atoms replaceable with fluorine;

"nearly perfluorinated" (for example, in reference to a group or moiety) means almost completely fluorinated such that there is only one carbon-bonded hydrogen atom replaceable with fluorine in the moiety; and "substituted" means, for a chemical species, group or moiety, substituted by conventional substituents which do not interfere with the desired product or process, e.g., substituents can be alkyl, perfluoroalkyl, alkoxy, perfluoroalkoxy, aryl, phenyl, halo (F, Cl, Br, I), cyano, nitro, etc.

DETAILED DESCRIPTION

The present disclosure provides a novel class of hydrofluoroacetal compounds and novel methods for their synthesis and use.

Hydrofluoroacetal Compounds

The present disclosure provides a novel class of hydrofluoroacetal compounds according to the formula:

$$R_f^1[CH(\!-\!O\!-\!CH_{(3-m)}R_f^2{}_m)(\!-\!O\!-\!CF_2\!-\!CFH\!-\!R_f^3)]_n \quad [I]$$

In formula I, n can be 1 or 2 but is typically 1. In formula I, m can be 1, 2 or 3, typically 1 or 2, and most typically 1. Embodiments of this class of hydrofluoroacetal compounds include compounds according to formula 1 where m and n have the following combinations of values: n=1 and m=1; n=1 and m=2; n=1 and m=3; n=2 and m=1; n=2 and m=2; n=2 and m=3.

In formula I, $R_f^1$ is monovalent when n is 1 and bivalent when n is 2. When n is 1, $R_f^1$ is selected from the group consisting of fluorinated (typically highly fluorinated) alkyl groups which are linear, branched, cyclic, or a combination thereof, which may optionally be substituted, and which may optionally contain one or more catenated heteroatoms. In some embodiments the monovalent $R_f^1$ is selected from the group consisting of perfluorinated and nearly perfluorinated C1-C4 alkyl groups which may optionally contain one or more catenated oxygen atoms. Typical monovalent $R_f^1$ groups include $CF_3$—, $C_2F_5$—, $HCF_2CF_2$—, $CF_3CFHCF_2$—, n-$C_3F_7$—, iso-$C_3F_7$—, n-$C_4F_9$—, iso-$C_4F_9$—, and most typically $CF_3$— and $C_2F_5$—. When n is 2, $R_f^1$ is selected from the group consisting of fluorinated (typically highly fluorinated) alkylene groups which are linear, branched, cyclic, or a combination thereof, which may optionally be substituted, and which may optionally contain one or more catenated heteroatoms. In some embodiments the bivalent $R_f^1$ is selected from the group consisting of perfluorinated and nearly perfluorinated C1-C4 alkylene groups which may optionally contain one or more catenated oxygen atoms. Typical bivalent $R_f^1$ groups include —$CF_2$—, —$C_2F_4$—, n- or iso-—$C_3F_6$—, n- or iso-—$C_4F_8$—, and most typically —$C_2F_4$— and —$C_3F_6$—. $R_f^1$ may be fluorinated, highly fluorinated, nearly perfluorinated or perfluorinated and most typically highly fluorinated.

In formula I, each $R_f^2$ is independently selected from the group consisting of alkyl groups which are linear, branched, cyclic, or a combination thereof, which may optionally be substituted, and which may optionally contain one or more catenated heteroatoms. At least one $R_f^2$ is highly fluorinated, therefore, when m=1, $R_f^2$ is highly fluorinated, when m=2 one $R_f^2$ may be non-fluorinated and when m=3 two $R_f^2$ groups may be non-fluorinated. In some embodiments $R_f^2$ groups are independently selected from the group consisting of perfluorinated and nearly perfluorinated C1-C4 alkyl groups which may optionally contain one or more catenated oxygen atoms. In some embodiments, $R_f^2$ groups include oxygen hetero atoms (e.g. ether linkages). In some embodiments, $R_f^2$ groups include no heteroatoms. Typical fluorinated $R_f^2$ groups include $CF_3$—, $C_2F_5$—, n- or iso-$C_3F_7$—, n- or iso-$C_4F_9$—, $C_2F_4H$, $CF_2CFHCF_3$, n- or iso-$C_4F_8H$—, and most typically $CF_3$— or $C_2F_5$—. $R_f^2$ groups are typically nearly perfluorinated or perfluorinated and most typically perfluorinated. Typical non-fluorinated $R_f^2$ groups include $CH_3$— and $C_2H_5$— of which $CH_3$— is most typical.

In formula I, each $R_f^3$ is independently selected from the group consisting of fluorine and highly fluorinated alkyl groups which are linear, branched, cyclic, or a combination thereof, which may optionally be substituted, and which may optionally contain one or more catenated heteroatoms. In some embodiments $R_f^3$ groups are independently selected from the group consisting of perfluorinated and nearly perfluorinated C1-C4 alkyl groups which may optionally contain one or more catenated oxygen atoms. In some embodiments, $R_f^3$ groups include oxygen hetero atoms (e.g. ether linkages). In some embodiments, $R_f^3$ groups include no heteroatoms. Typical $R_f^3$ groups include F—, $CF_3$—, $C_2F_5$—, n-$C_3F_7$—, iso-$C_3F_7$—, n-$C_4F_9$—, iso-$C_4F_9$—, $CF_3O$—, $C_2F_5O$—, n-$C_3F_7O$—, iso-$C_3F_7O$—, n-$C_4F_9O$—, iso-$C_4F_9O$—, $CF_3OCF_2CF_2CF_2O$—, $C_3F_7OCF(CF_3)CF_2O$—, More typically, $R_f^3$ is selected from F, $CF_3$—, $CF_3O$—, $CF_3OCF_2CF_2CF_2O$—, and $C_3F_7O$— and most typically $CF_3$—. $R_f^3$ groups are typically nearly perfluorinated or perfluorinated and most typically perfluorinated.

The hydrofluoroacetal compounds according to the formula:

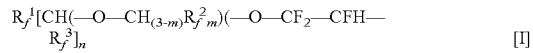

typically contain at least two chiral carbons, e.g., the first carbon from the left designated "C" in formula I. In some embodiments, the compound is present as a mixture of diastereomers. In some embodiments, the compound is present as a single enantiomer or a mixture enriched in a single enantiomer. In some embodiments, the compound is present as the (+)-enantiomer or a mixture enriched in the (+)-enantiomer. In some embodiments, the compound is present as the (−)-enantiomer or a mixture enriched in the (−)-enantiomer. The enantiomers may be separated by any suitable method, which may include gas chromatography on a chiral stationary phase. In some embodiments, the compound is present as the enantiomer(s) which exhibit (R)-enantiomeric form at each carbon marked with an asterisk in formula I':

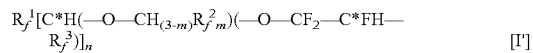

or a mixture enriched in such enantiomers. In some embodiments, the compound is present as the enantiomer(s) which exhibit (S)-enantiomeric form at each carbon marked with an asterisk in formula I', or a mixture enriched in such enantiomers. In some embodiments, the compound is present as the enantiomer(s) which exhibit (S)-enantiomeric form at one carbon marked with an asterisk in formula I' and (R)-enantiomeric form at the other, or a mixture enriched in such enantiomers. The enantiomers may be separated by any suitable method, which may include gas chromatography on a chiral stationary phase. Diastereomers may be separated by any suitable method, which may include gas chromatography or distillation.

Representative embodiments of the class of hydrofluoroacetal compounds provided by the present disclosure include the following:

$CF_3CH(OCH_2CF_3)OCF_2CFHCF_3$
$CF_3CH(OCH(CF_3)_2)OCF_2CFHCF_3$
$CF_3CH(OCH_2CF_2CF_3)OCF_2CFHCF_3$
$CF_3CH(OCH(CF_2CF_3)CF(CF_3)_2)OCF_2CFHCF_3$
$CF_3CH(OCH_2CF_3)OCF_2CFHCF_2CF_3$
$CF_3CH(OCH(CF_3)_2)OCF_2CFHCF_2CF_3$
$CF_3CH(OCH_2CF_2CF_3)OCF_2CFHCF_2CF_3$
$CF_3CH(OCH(CF_2CF_3)CF(CF_3)_2)OCF_2CFHCF_2CF_3$
$CF_3CF_2CH(OCH_2CF_3)OCF_2CFHCF_3$
$CF_3CF_2CH(OCH(CF_3)_2)OCF_2CFHCF_3$
$CF_3CF_2CH(OCH_2CF_2CF_3)OCF_2CFHCF_3$
$CF_3CF_2CH(OCH(CF_2CF_3)CF(CF_3)_2)OCF_2CFHCF_3$
$CF_3CF_2CH(OCH_2CF_3)OCF_2CFHCF_2CF_3$
$CF_3CF_2CH(OCH(CF_3)_2)OCF_2CFHCF_2CF_3$
$CF_3CF_2CH(OCH_2CF_2CF_3)OCF_2CFHCF_2CF_3$
$CF_3CF_2CH(OCH(CF_2CF_3)CF(CF_3)_2)OCF_2CFHCF_2CF_3$
$CF_3CH(OCH_2CF_3)OCF_2CFHOCF_3$
$CF_3CH(OCH(CF_3)_2)OCF_2CFHOCF_3$
$CF_3CH(OCH(CF_2CF_3)CF(CF_3)_2)OCF_2CFHOCF_3$
$CF_3CH(OCH(CF_2CF_3)_2)OCF_2CFHOCF_3$
$CF_3CH(OCH_2CF_3)OCF_2CFHOCF_2CF_3$
$CF_3CH(OCH_2CF_2CF_3)OCF_2CFHOCF_2CF_3$
$CF_3CH(OCH_2CF_3)OCF_2CFHOCF_2CF_2CF_3$
$CF_3CH(OCH(CF_3)_2)OCF_2CFHOCF_2CF_2CF_3$ $CF_3CH(OCH_2CF_2CF_3)OCF_2CFHOCF_2CF_2CF_3$
$CF_3CH(OCH(CF_2CF_3)CF(CF_3)_2)OCF_2CFHOCF_2CF_2CF_3$
$CF_3CF_2CH(OCH_2CF_3)OCF_2CFHOCF_3$
$CF_3CF_2CH(OCH(CF_3)_2)OCF_2CFHOCF_3$
$CF_3CF_2CH(OCH_2CF_2CF_3)OCF_2CFHOCF_3$
$CF_3CF_2CH(OCH(CF_2CF_3)CF(CF_3)_2)OCF_2CFHOCF_3$
$CF_3CF_2CH(OCH_2CF_3)OCF_2CFHOCF_2CF_3$
$CF_3CF_2CH(OCH(CF_3)_2)OCF_2CFHOCF_2CF_3$
$CF_3CF_2CH(OCH_2CF_2CF_3)OCF_2CFHOCF_2CF_3$
$CF_3CF_2CH(OCH(CF_2CF_3)CF(CF_3)_2)OCF_2CFHOCF_2CF_3$
$CF_3CH(OCH_2CF_2CFHOCF_3)OCF_2CFHCF_3$
$CF_3CH(OCH_2CF_2CFHOCF_2CF_2CF_3)OCF_2CFHCF_3$
$CF_3CH(OCH_2CF_2CFHOCF_3)OCF_2CFHCF_2CF_3$
$CF_3CH(OCH_2CF_2CFHOCF_2CF_2CF_3)OCF_2CFHCF_2CF_3$
$CF_3CF_2CH(OCH_2CF_2CFHOCF_3)OCF_2CFHCF_3$
$CF_3CF_2CH(OCH_2CF_2CFHOCF_2CF_2CF_3)OCF_2CFHCF_3$
$CF_3CF_2CH(OCH_2CF_2CFHOCF_3)OCF_2CFHCF_2CF_3$
$CF_3CF_2CH(OCH_2CF_2CFHOCF_2CF_2CF_3)OCF_2CFHCF_2CF_3$
$CF_3CH(OCH_2CF_2CFHOCF_3)OCF_2CFHOCF_3$
$CF_3CH(OCH_2CF_2CFHOCF_3)OCF_2CFHOCF_2CF_3$
$CF_3CH(OCH_2CF_2CFHOCF_2CF_2CF_3)OCF_2CFHOCF_3$
$CF_3CH(OCH_2CF_2CFHOCF_3)OCF_2CFHOCF_2CF_2CF_3$
$CF_3CH(OCH_2CF_2CFHOCF_2CF_2CF_3)OCF_2CFHOCF_2CF_3$
$CF_3CF_2CH(OCH_2CF_2CFHOCF_3)OCF_2CFHOCF_3$
$CF_3CF_2CH(OCH_2CF_2CFHOCF_2CF_2CF_3)OCF_2CFHOCF_3$
$CF_3CF_2CH(OCH_2CF_2CFHOCF_3)OCF_2CFHOCF_2CF_3$
$CF_3CF_2CH(OCH_2CF_2CFHOCF_2CF_2CF_3)OCF_2CFHOCF_2CF_3$
$CF_3CH(OCH_2CF_3)OCF_2CHF_2$
$CF_3CH(OCH(CF_3)_2)OCF_2CHF_2$
$CF_3CH(OCH_2CF_2CF_3)OCF_2CHF_2$
$CF_3CH(OCH(CF_2CF_3)CF(CF_3)_2)OCF_2CHF_2$
$CF_3CF_2CH(OCH_2CF_3)OCF_2CHF_2$
$CF_3CF_2CH(OCH(CF_3)_2)OCF_2CHF_2$
$CF_3CF_2CH(OCH_2CF_2CF_3)OCF_2CHF_2$
$CF_3CF_2CH(OCH(CF_2CF_3)CF(CF_3)_2)OCF_2CHF_2$
$CF_3CH(OCH_2CF_3)OCF_2CFHOCF_2CF_2CF_2OCF_3$
$CF_3CH(OCH(CF_3)_2)OCF_2CFHOCF_2CF_2CF_2OCF_3$
$CF_3CH(OCH_2CF_2CF_3)OCF_2CFHOCF_2CF_2CF_2OCF_3$
$CF_3CH(OCH(CF_2CF_3)CF(CF_3)_2)OCF_2CFHOCF_2CF_2CF_2OCF_3$
$CF_3CH(OCH_2CF_2CF_3)OCF_2CFHOCF_2CF(CF_3)OCF_2CF_2CF_3$
$CF_3CH(OCH(CF_3)_2)OCF_2CFHOCF_2CF(CF_3)OCF_2CF_2CF_3$
$CF_3CH(OCH_2CF_2CF_3)OCF_2CFHOCF_2CF(CF_3)OCF_2CF_2CF_3$
$CF_3CH(OCH(CF_2CF_3)CF(CF_3)_2)OCF_2CFHOCF_2CF(CF_3)OCF_2CF_2CF_3$
$CF_3CH(OCH_2CF_2CFHCF_3)OCF_2CFHCF_3$
$CF_3CH(OCH(CH_3)CF_2CFHCF_3)OCF_2CFHCF_3$
$CF_3CH(OC(CH_3)_2CF_2CFHCF_3)OCF_2CFHCF_3$
$CF_3CF_2CH(OCH_2CF_2CFHCF_3)OCF_2CFHCF_3$
$CF_3CF_2CH(OCH(CH_3)CF_2CFHCF_3)OCF_2CFHCF_3$
$CF_3CF_2CH(OC(CH_3)_2CF_2CFHCF_3)OCF_2CFHCF_3$
$CF_3CH(OCH_2CF_2CFHCF_3)OCF_2CFHOCF_3$
$CF_3CH(OCH(CH_3)CF_2CFHCF_3)OCF_2CFHOCF_3$
$CF_3CH(OC(CH_3)_2CF_2CFHCF_3)OCF_2CFHOCF_3$
$CF_3CF_2CH(OCH_2CF_2CFHCF_3)OCF_2CFHOCF_3$
$CF_3CF_2CH(OCH(CH_3)CF_2CFHCF_3)OCF_2CFHOCF_3$
$CF_3CF_2CH(OC(CH_3)_2CF_2CFHCF_3)OCF_2CFHOCF_3$
$CF_3CH(OCH_2CF_2CF_2H)OCF_2CFHCF_3$
$CF_3CH(OCH_2C_4F_8H)OCF_2CFHCF_3$
$CF_3CH(OCH_2CF_2CF_2H)OCF_2CFHOCF_3$
$CF_3CH(OCH_2C_4F_8H)OCF_2CFHOCF_3$
$CF_3CH_2OCH(OCF_2CFHCF_3)CF_2CF_2CH(OCF_2CFHCF_3)OCH_2CF_3$
$CF_3CH_2OCH(OCF_2CFHCF_3)CF_2CF_2CH(OCF_2CFHCF_3)OCH_2C_2F_5$
$CF_3CFHCF_2CH_2OCH(OCF_2CFHCF_3)CF_2CF_2CH(OCF_2CFHCF_3)$—$OCH_2CF_2CFHCF_3$
$CF_3CH_2OCH(OCF_2CFHCF_3)CF_2CF_2CH(OCF_2CFHOCF_3)OCH_2CF_3$
$CF_3CH(OCF_2CFHCF_3)OCH_2CF_2CF_2CH_2OCH(CF_3)OCF_2CFHCF_3$
$CF_3CH(OCF_2CFHOCF_3)OCH_2CF_2CF_2CH_2OCH(CF_3)OCF_2CFHOCF_3$
$HCF_2CF_2CH(OCH_2CF_3)OCF_2CFHCF_3$
$CF_3CFHCF_2CH(OCH_2CF_3)OCF_2CFHCF_3$

Embodiments of the class of hydrofluoroacetal compounds provided by the present disclosure have demonstrated surprising stability when challenged with both water and dilute aqueous acid treatment.

Preparation of Hydrofluoroacetal Compounds

The novel class of hydrofluoroacetal compounds according to the present disclosure may be made according to any suitable method. In some embodiments, hydrofluoroacetal compounds according to the present disclosure may be prepared according to the methods disclosed following.

In some embodiments, hydrofluoroacetal compounds according to formula I may be made by reacting a fluorinated hemiacetal compound with a fluorinated alkene. In some embodiments, hydrofluoroacetal compounds according to formula I may be made by a method including the step of reacting a compound according to the formula:

$$R_f^1[CH(\text{—}O\text{—}CH_{(3-m)}R_{f\,m}^2)(\text{—}OH)]_n \qquad [II]$$

with one or more compounds according to the formula:

$$CF_2\text{=}CF\text{—}R_f^3 \qquad [III]$$

wherein n, m, $R_f^1$, $R_f^2$ and $R_f^3$ are as defined with regard to formula I.

Any suitable reaction conditions may be used. In some embodiments, this reaction step may be performed under conditions of controlled and/or elevated temperature, in some cases 30-50° C. In some embodiments, this reaction step may be performed under conditions of reduced pressure or inert atmosphere. The reaction step may be performed in any suitable solvent, typically a solvent that is inert to the reaction, or neat. In some embodiments, this reaction step may be performed in the presence of a catalyst. Most typically, the catalyst is potassium carbonate.

As demonstrated in the Examples, this reaction step can be performed without appreciable decomposition of the hemiacetal reactant in spite of treatment with an inorganic base. This result is remarkable, since the hemiacetal comprises a relatively good leaving group in the fluorinated alkoxide moiety. Furthermore, in many embodiments including some demonstrated in the Examples, the hydrofluoroacetal compounds made according to this method may be free or substantially free of olefins, obviating the need for a further chemical treatment (e.g. treatment with anhydrous HF) to remove them.

The reactants according to formulas II and III may be obtained from any suitable source or synthesized in any suitable manner. In some embodiments, the reactant according to formula II is made by reaction of a fluorinated aldehyde with a fluorinated alcohol. In some embodiments, the reactant according to formula II is made by conversion of a fluorinated hemiacetal into a fluorinated aldehyde followed by reaction with a fluorinated alcohol.

In some embodiments, the reactant according to formula II is made by a method including the step of reacting a compound according to the formula:

$$R_f^1[CHO]_n \quad\quad [V]$$

with one or more compounds according to the formula:

$$HO-CH_{(3-m)}R_f^2{}_m \quad\quad [VI]$$

wherein n, m, $R_f^1$, $R_f^2$ and $R_f^3$ are as defined above.

Any suitable reaction conditions may be used. In some embodiments, this reaction step may be performed under conditions of controlled and/or elevated temperature. The reaction step may be performed in any suitable solvent, typically a solvent that is inert to the reaction such as acetonitrile, or neat.

In some embodiments, the reactant according to formula II is made by a method including the step of reacting a compound according to the formula:

$$R_f^1[CH(OR)OH]_n \quad\quad [IV]$$

with a dehydrating agent such as sulfuric acid to form a compound according to the formula:

$$R_f^1[CHO]_n \quad\quad [V]$$

and further reacting V with one or more compounds according to the formula:

$$HO-CH_{(3-m)}R_f^2{}_m \quad\quad [VI]$$

wherein n, m, $R_f^1$, $R_f^2$, $R_f^3$ and R are as defined above and R is selected from the group consisting of alkyl groups which are linear, branched, cyclic, or a combination thereof, which may optionally be substituted, and which may optionally contain one or more catenated heteroatoms. In some embodiments R is selected from the group consisting of C1-C4 alkyl groups which may optionally contain one or more catenated oxygen atoms. Typically, R is methyl or ethyl.

Any suitable reaction conditions may be used. In some embodiments, the compound according to formula V is formed in a first reaction chamber and distilled from the first reaction chamber upon formation into a second reaction chamber where the compound according to formula II is formed. In such embodiments, suitable distillation, heating and condensing equipment may be used. In some embodiments, the compound according to formula IV may be added slowly or dropwise to the first reaction chamber, which may be preloaded with the dehydrating agent. This reaction step may be performed under conditions of controlled and/or elevated temperature, in some cases 60-90° C. or higher, so as to drive the reaction or provide distillation of the product from the reaction mixture or both. This reaction step may be performed in any suitable solvent, typically a solvent that is inert to the reaction, or neat. In some embodiments, the compound according to formula V is distilled into the second reaction chamber which is preloaded with the compound according to formula VI. Any suitable reaction conditions may be used in the second reaction chamber. In some embodiments, this reaction step may be performed under conditions of controlled and/or elevated temperature. The reaction step may be performed in any suitable solvent, typically a solvent that is inert to the reaction, or neat.

In some embodiments, the resulting product may then be separated into particular enantiomers or diastereomers or mixtures enriched or depleted in particular enantiomers or diastereomers. The enantiomers or diastereomers may be separated by any suitable method, which may include gas chromatography, gas chromatography on a chiral column, or distillation.

Use of Hydrofluoroacetal Compounds

The hydrofluoroacetal compounds of this disclosure (or a normally liquid composition comprising, consisting, or consisting essentially thereof) can be used in various applications where chlorofluorocarbons (CFCs) have been used. CFCs are currently disfavored and regulated due to the adverse effects that CFCs are believed to have on the environment. For example, the compounds can be used as solvents for precision or metal cleaning of electronic articles such as disks or circuit boards; as heat transfer agents; as cell size regulators in making foam insulation (for example, polyurethane, phenolic, and thermoplastic foams); as chemical fire extinguishing agents in streaming applications; as carrier fluids or solvents for document preservation materials and for lubricants; as power cycle working fluids such as for heat pumps; as inert media for polymerization reactions; as displacement drying agents for removing water, such as from jewelry or metal parts; as resist developers in conventional circuit manufacturing techniques including chlorine-type developing agents; as strippers for photoresists when used with, for example, a chlorohydrocarbon such as 1,1,1-trichloroethane or trichloroethylene, and in tissue or biological specimen preservation, e.g., as a replacement for formaldehyde. In these applications, diastereomeric mixtures of these hydrofluoroacetal compounds can typically be used without any further resolution into enantiomeric forms, however, in some embodiments a single enantiomer may be used.

The hydrofluoroacetal compounds typically exhibit high dielectric strengths (for example, greater than about $10^8$ ohm-cm), which can make them well-suited for use in the semiconductor industry. The hydrofluoroacetal compounds that exhibit unexpectedly high thermal stabilities can be particularly useful in high temperature applications such as in heat transfer applications in the semiconductor industry and in flat screen panel manufacture.

The hydrofluoroacetal compounds can be used alone or in admixture with each other or with other commonly-used solvents (for example, alcohols, ethers, alkanes, alkenes, perfluorocarbons, perfluorinated tertiary amines, perfluoroethers, cycloalkanes, esters, ketones, aromatics, siloxanes, hydrochlorocarbons, hydrochlorofluorocarbons, hydrofluorocarbons, and the like, and mixtures thereof). Such co-solvents can be chosen to modify or enhance the properties of a composition for a particular use and can be utilized in ratios (of co-solvent(s) to hydrofluoroacetal(s)) such that the resulting composition preferably has no flash point. If desired, the hydrofluoroacetal compounds can be used in combination with other compounds that are very similar in properties relative to a particular use (for example, other hydrofluoroacetal compounds) to form compositions that "consist essentially" of the hydrofluoroacetal compounds of this disclosure.

Minor amounts of optional components can be added to the compounds to impart particular desired properties for particular uses. Useful compositions can comprise conventional additives such as, for example, surfactants, coloring agents, stabilizers, anti-oxidants, flame retardants, and the like, and mixtures thereof.

The hydrofluoroacetal compounds are useful as solvents for cleaning and drying applications such as, for example, those described in U.S. Pat. No. 5,125,089 (Flynn et al.), U.S. Pat. No. 3,903,012 (Brandreth), U.S. Pat. No. 4,169,807 (Zuber), and U.S. Pat. No. 5,925,611 (Flynn et al.), the descriptions of which are incorporated herein by reference. Both organic and inorganic substrates can be cleaned by contacting them with a composition comprising at least one HFE of this disclosure. Most contaminants can be removed, including hydrocarbon contaminants, fluorocarbon contaminants, particulates, and water.

In using the compounds for the drying of or displacing water from the surface of articles (such as circuit boards), any suitable process may be used, for example, the process of drying or water displacement described in U.S. Pat. No. 5,125,978 (Flynn et al.). Broadly, such process comprises contacting the surface of an article with a liquid composition comprising at least one hydrofluoroacetal compound of this disclosure, preferably in admixture with a non-ionic fluoroaliphatic surface active agent. The wet article is immersed in the liquid composition and agitated therein, the displaced water is separated from the liquid composition, and the resulting water-free article is removed from the liquid composition. Further description of the process and the articles that can be treated can be found in said U.S. Pat. No. 5,125,978, which description is incorporated herein.

In using the compounds of this disclosure in vapor phase soldering, any suitable process may be used, for example, the process described in U.S. Pat. No. 5,104,034 (Hansen), which description is incorporated herein. Briefly, such process comprises immersing a component to be soldered in a body of vapor comprising at least one hydrofluoroacetal compound of this disclosure to melt the solder. In carrying out such a process, a liquid pool of a hydrofluoroacetal composition is heated to boiling in a tank to form a saturated vapor in the space between the boiling liquid and a condensing means, a workpiece to be soldered is immersed in the vapor whereby the vapor is condensed on the surface of the workpiece so as to melt and reflow the solder, and the soldered workpiece is then removed from the space containing the vapor.

In using the compounds of this disclosure as cell size regulators in making plastic foam (such as foamed polyurethane), any suitable process may be used, for example, the process reactants and reaction conditions described in U.S. Pat. No. 5,210,106 (Dams et al.) and U.S. Pat. No. 5,539,008 (Dams et al.), which descriptions are incorporated herein. One such process comprises vaporizing a blowing agent mixture in the presence of at least one foamable polymer or the precursors of at least one foamable polymer, the blowing agent mixture comprising at least one hydrofluoroacetal compound of this disclosure.

In using the compounds of this disclosure as heat transfer agents, any suitable process may be used, for example, the processes described in U.S. Reissue Pat. No. 37,119 E (Sherwood) and U.S. Pat. No. 6,374,907 B1 (Tousignant et al.), which descriptions are incorporated herein. In carrying out such processes, heat is transferred between a heat source (for example, a silicon wafer or a component of a flat panel display) and a heat sink through the use of a heat transfer agent comprising at least one hydrofluoroacetal compound of this disclosure.

In using the hydrofluoroacetal compounds of this disclosure as deposition solvents in coating applications or in document preservation applications, any suitable process may be used, for example, the processes described in U.S. Pat. No. 5,925,611 (Flynn et al.) and U.S. Pat. No. 6,080,448 (Leiner et al.), which descriptions are incorporated herein. Such processes for depositing a coating on a substrate (for example, magnetic recording media or cellulose-based materials) comprises applying, to at least a portion of at least one surface of the substrate, a composition comprising (a) a solvent composition comprising at least one hydrofluoroacetal compound of this disclosure; and (b) at least one coating material that is soluble or dispersible in the solvent composition. Coating materials that can be deposited by the process include pigments, lubricants, stabilizers, adhesives, anti-oxidants, dyes, polymers, pharmaceuticals, release agents, inorganic oxides, document preservation materials (for example, alkaline materials used in the deacidification of paper), and the like, and combinations thereof. Preferred materials include perfluoropolyether, hydrocarbon, and silicone lubricants; amorphous copolymers of tetrafluoroethylene; polytetrafluoroethylene; document preservation materials; and combinations thereof. Most preferably, the material is a perfluoropolyether or a document preservation material.

In using the hydrofluoroacetal compounds of this disclosure as fire extinguishing and prevention agents, any suitable process may be used, for example, the processes described in U.S. Pat. No. 5,718,293 (Flynn et al.), which descriptions are incorporated herein. Such process for the extinction of fires comprises applying or introducing to a fire a composition comprising at least one hydrofluoroacetal compound of this disclosure. The hydrofluoroacetal compounds of this disclosure can be used alone or in combination with other commonly-used fire extinguishing or prevention agents.

In using the hydrofluoroacetal compounds of this disclosure in cutting or abrasive working operations, any suitable process may be used, for example, the processes described in, U.S. Pat. No. 6,759,374 (Milbrath et al.), the descriptions of which are incorporated herein. Such a process for metal, cermet, or composite working comprises applying a working fluid to a metal, cermet, or composite workpiece and tool, the working fluid comprising at least one hydrofluoroacetal compound of this disclosure and at least one lubricious additive. The working fluid can further comprise one or more conventional additives (for example, corrosion inhibitors, antioxidants, defoamers, dyes, bactericides, freezing point depressants, metal deactivators, co-solvents, and the like, and mixtures thereof).

In using the hydrofluoroacetal compounds of this disclosure as polymerization media or as chain transfer agents, any suitable process may be used, for example, the processes described in, Research Disclosures, Number 40576, page 81 (January 1998) and in U.S. Pat. No. 5,182,342 (Feiring et al.) and U.S. Pat. No. 6,399,729 (Farnham et al.), the descriptions of which are incorporated herein. Such processes comprise polymerizing at least one monomer (preferably, at least one fluorine-containing monomer) in the presence of at least one polymerization initiator and at least one hydrofluoroacetal compound of this disclosure.

Objects and advantages of this disclosure are further illustrated by the following examples, but the particular materials and amounts thereof recited in these examples, as well as other conditions and details, should not be construed to unduly limit this disclosure.

EXAMPLES

Unless otherwise noted, all reagents were obtained or are available from Aldrich Chemical Co., Milwaukee, Wis., or may be synthesized by known methods.

In the following examples, mixtures of diastereomers were obtained due to the presence of two (or more) optical centers in the molecules. These diastereomers were separated by gas chromatography where noted.

Example 1

Preparation of $CF_3CH(OCH_2CF_3)OCF_2CFHCF_3$

Part 1: Synthesis of $CF_3CH(OH)OCH_2CF_3$

A 250 mL round bottom flask was equipped with a thermometer, magnetic stir bar, addition funnel and dry ice condenser leading to a receiver cooled with an isopropanol cold bath held at about −30° C. by the addition of portions of dry ice as needed. Sulfuric acid (175 g) was placed in the 250 mL flask and $CF_3CH_2OH$ (Aldrich, 57.8 g, 0.578 mole) placed in the receiver. Trifluoroacetaldehyde methyl hemiacetal (Alfa Aesar, 50 g, 90% purity, 0.346 mole) was placed in the addition funnel and added rapidly dropwise to the sulfuric acid solution which was heated to 75° C. as the addition proceeded. The aldehyde began to distill from the sulfuric acid solution at a pot temperature of about 64° C. After the completion of the addition the sulfuric acid solution was held at 75° C. for an additional hour. The receiver had gained 26.3 g in weight and this solution was used without purification in the next step.

Part 2: Reaction with $CF_3CF=CF_2$

The entire contents of the receiver (containing the desired $CF_3CH(OH)OCH_2CF_3$ as a solution in trifluoroethanol) was placed in a 600 mL Parr reaction vessel along with acetonitrile (167 g) and powdered potassium carbonate (3.0 g). The reactor was sealed and evacuated by connecting the reactor to an aspirator and a nitrogen source by a firestone valve, which was turned to the aspirator and then the nitrogen source in four repetitions, ending with the aspirator. The reactor was then heated to 40° C. Hexafluoropropene (100 g, 0.67 mole) was added in portions over several hours and the reactor then held at temperature (40° C.) for an additional 3.5 hours. The reactor was then allowed to cool to room temperature overnight. The reactor was then opened and the contents transferred to a separatory funnel with the addition of water. The lower fluorochemical phase was separated and washed twice with water and once with saturated sodium chloride brine and the product distilled two times in a concentric tube distillation column. The product distilled at 119° C. as a mixture of diastereomers which were easily separated by GLC. The product identity was confirmed by GC-MS and H-1 and F-19 NMR as a mixture of diastereomers in a ratio of 57/43%. One diastereomeric fraction was thought to contain SS and RR enantiomers and the other SR and RS enantiomers. The nmr data showed that the product contained about 16.7% olefin [—$OCF=CFCF_3$] as a 47/53% cis/trans mixture. Treatment of this material with anhydrous HF (essentially as described in U.S. Patent Publication No. 2005/0127322 Costello et al.) at ambient temperature served to completely remove both olefins converting them to the desired product. The excess trifluoroethanol was converted to $CF_3CH_2OCF_2CFHCF_3$ which was removed during the distillation.

Stability Testing Protocol 1:

$CF_3CH(OCH_2CF_3)OCF_2CFHCF_3$ (5.2 g) was treated with DI water (20 g) at 50° C. for 6 hours and ambient temperature for an additional 18 hours. The lower phase (4.2 g, 81%) was separated and GLC analysis showed a purity of 99.8% (essentially the same as the starting material) and no indication of any formation of trifluoroethanol. The upper aqueous phase contained a trace of trifluoroethanol.

Stability Testing Protocol 2:

$CF_3CH(OCH_2CF_3)OCF_2CFHCF_3$ (4.3 g) was treated with DI water (20 g) containing a drop of 50% aqueous hydrochloric acid at 50° C. for 6 hours and ambient temperature for an additional 12 hours. The GLC of the lower recovered fluorochemical phase (3.7 g, 86%) showed that the acetal was still intact with a purity of 99.7%. The remaining upper aqueous phase contained some pentafluoropropanol but the amount, though larger than in the neutral hydrolysis reaction, was still small.

Example 2

Preparation of $CF_3CH(OCH_2C_2F_5)OCF_2CFHCF_3$

Part 1: Synthesis of $CF_3CH(OH)OCH_2C_2F_5$

This reaction was carried out in the same manner as described in Example 1 using charges of sulfuric acid (175 g), $C_2F_5CH_2OH$ (86.7 g, 0.578 mole) and trifluoroacetaldehyde methyl hemiacetal (Alfa Aesar, 50 g, 90% purity, 0.346 mole). The receiver gained 27.1 g in weight and this solution was used without purification in the next step.

Part 2: Reaction with $CF_3CF=CF_2$

The entire contents of the receiver (containing the desired $CF_3CH(OH)OCH_2C_2F_5$ as a solution in pentafluoropropanol) was placed in a 600 mL Parr reaction vessel along with acetonitrile (162 g) and powdered potassium carbonate (3.4 g). The reactor was sealed, evacuated as described in Example 1, and heated to 40° C. Hexafluoropropene (117 g, 0.78 mole) was added in portions over one hour and the reactor then held at temperature (40° C.) overnight. The reaction mixture was worked up as described in Example 1 and distilled to give a main fraction of boiling range 128-129° C. as a mixture of two diastereomers which were separable by GLC. The product identity was confirmed by GC-MS and H-1 and F-19 NMR as a mixture of diastereomers in a ratio of 53/47%. One diastereomeric fraction was thought to contain SS and RR enantiomers and the other SR and RS enantiomers. The nmr data showed that the product contained about 23.3% olefin [$OCF=CFCF_3$] also as a 51/49% cis/trans mixture. The excess pentafluoropropanol was converted to $CF_3CF_2CH_2OCF_2CFHCF_3$ which was removed during the distillation.

Example 3

Preparation of $C_2F_5CH(OCH_2C_2F_5)OCF_2CFHCF_3$ $C_2F_5CHO$ was prepared by reduction of $C_2F_5CO_2CH_2C_2F_5$ with $NaAlH_2(OC_2H_4OCH_3)_2$ in THF followed by distillation from concentrated sulfuric acid. The aldehyde was distilled directly into $C_2F_5CH_2OH$ as described in Example 2 to yield a solution of $C_2F_5CH(OH)OCH_2C_2F_5$ in pentafluoropropanol (weight gain of 14.0 g in the pentafluoropropanol solution).

The entire contents of the pentafluoropropanol solution (containing the desired $C_2F_5CH(OH)OCH_2C_2F_5$) were placed in a 600 mL Parr reaction vessel along with acetonitrile (167 g) and powdered potassium carbonate (2.9 g). The reactor was sealed, evacuated and heated to 40° C. Hexafluoropropene (64.8 g, 0.43 mole) was added in portions over about two hours and the reactor then held at temperature overnight. The reaction mixture was worked up by pouring into water and washing the resulting lower phase three times with water followed by distillation. The distillation afford a main fraction of boiling point 142° C. The product identity was confirmed by GC-MS and H-1 and F-19 NMR as a mixture of diastereomers in a ratio of 55/45%. One diastereomeric fraction was thought to contain SS and RR enantiomers and the other SR and RS enantiomers. The NMR data showed that the product contained about 4.2% olefin [—$OCF=CFCF_3$] as a 43/57% cis/trans mixture. The excess pentafluoropropanol was converted to $CF_3CF_2CH_2OCF_2CFHCF_3$ which was removed during the distillation.

Example 4

Preparation of $CF_3CH(OCH_2C_4F_8H)OCF_2CFHCF_3$

Part 1: Synthesis of $CF_3CH(OH)OCH_2C_4F_8H$

This reaction was carried out in the same manner as described in Example 1 using charges of sulfuric acid (175 g), $HC_4F_8CH_2OH$ (97.4 g, 0.42 mole, available from Daikin) and trifluoroacetaldehyde methyl hemiacetal (Alfa Aesar, 50 g, 90% purity, 0.346 mole). The receiver had gained 25 g in weight and this solution was used without purification in the next step.

Part 2: Reaction with $CF_3CF=CF_2$

The entire contents of the receiver (containing the desired $CF_3CH(OH)OCH_2C_4F_8H$ as a solution in the excess $HC_4F_8CH_2OH$) was placed in a 600 mL Parr reaction vessel along with acetonitrile (170 g) and powdered potassium carbonate (3.0 g). The reactor was sealed, evacuated and heated to 40° C. Hexafluoropropene (88.2 g, 0.59 mole) was added in portions over one hour and the reactor then held at temperature (40° C.) overnight. The reaction mixture was worked up by pouring into water and washing the resulting lower phase three times with water followed by distillation. The main fraction had a boiling point of 181° C. The product identity was confirmed by GC-MS and H-1 and F-19 NMR as a mixture of diastereomers in a ratio of 53/47%. One diastereomeric fraction was thought to contain SS and RR enantiomers and the other SR and RS enantiomers. The NMR data showed that the product contained about 16% olefin [—$OCF=CFCF_3$] also as a 53/47% cis/trans mixture. The excess $HC_4F_8CH_2OH$ was converted to $HC_4F_8CH_2OCF_2CFHCF_3$ which was removed during the distillation.

Example 5

Preparation of $CF_3CH[OCH(CF_3)_2]OCF_2CFHCF_3$

Part 1: Synthesis of $CF_3CH(OH)OCH(CF_3)_2$

This reaction was carried out in essentially the same manner as described in Example 1 using charges of sulfuric acid (175 g), $(CF_3)_2CHOH$ (70.6 g, 0.42 mole, Synquest Labs) and trifluoroacetaldehyde methyl hemiacetal (Alfa Aesar, 50 g, 90% purity, 0.346 mole). In this case the receiver was cooled in an ice water bath to about 0° C. to avoid solidification of the alcohol. The receiver had gained 8.6 g in weight and this solution was used without purification in the next step.

Part 2: Reaction with $CF_3CF=CF_2$

The entire contents of the receiver (containing the desired $CF_3CH(OH)OCH(CF_3)_2$ as a solution in excess hexafluoroisopropanol) was placed in a 600 mL Parr reaction vessel along with acetonitrile (167 g) and powdered potassium carbonate (3.4 g). The reactor was sealed, evacuated and heated to 40° C. Hexafluoropropene (88 g, 0.59 mole) was added in portions over one hour and the reactor then held at temperature (40° C.) overnight. The reaction mixture was worked up by pouring into water and washing the resulting lower phase three times with water followed by distillation. The main fraction had a distillation range of 118-122° C. The product identity was confirmed by GC-MS and H-1 NMR. The nmr data showed that the product contained only 4.5% olefin [—$OCF=CFCF_3$] as a cis/trans mixture. The excess hexafluoroisopropanol was converted to $(CF_3)_2CHOCF_2CFHCF_3$ which was removed during the distillation.

Example 6

Preparation of $CF_3CH[OCH_2C_2F_5]OCF_2CFHOCF_3$

Part 1: Synthesis of $CF_3CH[OCH_2C_2F_5]OH$

This material was prepared as in Example 2, Part 1 but using only 63 g of $C_2F_5CH_2OH$. The receiver gained 25.4 g in weight and this solution was used without purification in the next step.

Part 2: Reaction with $CF_3OCF=CF_2$

The entire contents of the receiver (containing the desired $CF_3CH[OCH_2C_2F_5]OH$ as a solution in excess $C_2F_5CH_2OH$) was placed in a 600 mL Parr reaction vessel along with acetonitrile (170 g) and powdered potassium carbonate (3.1 g). The reactor was sealed, evacuated and heated to 40° C. Trifluoromethyl trifluorovinyl ether (76.7 g, 0.46 mole, SynQuest Labs) was added in portions over one hour and the reactor then held at temperature (40° C.) overnight. The reaction mixture was worked up by pouring into water and washing the resulting lower phase three times with water followed by distillation. The main fraction had a boiling point of 130° C. in a purity of 97.4% by GLC. The product identity was confirmed by GC-MS, IR and H-1 NMR. No olefin was observed. The excess pentafluoropropanol was converted to $CF_3CF_2CH_2OCF_2CFHCF_3$ which was removed during the distillation.

Example 7

Preparation of $CF_3CH[OCH_2CF_2CFHOC_3F_6OCF_3]OCF_2CFHCF_3$

Part 1: Synthesis of $CF_3CH[OCH_2CF_2CFHOC_3F_6OCF_3]OH$

This reaction was carried out in essentially the same manner as described in Example 1 using charges of sulfuric acid (175 g), $CF_3OC_3F_6OCFHCF_2CH_2OH$ (55 g, 78% purity, prepared by the free radical reaction of methanol with $CF_3OC_3F_6OCF=CF_2$) and trifluoroacetaldehyde methyl hemiacetal (Alfa Aesar, 18 g, 90% purity, 0.125 mole). The receiver had gained about 10 g in weight and this solution was used without purification in the next step.

Part 2: Reaction with $CF_3CF=CF_2$

The entire contents of the receiver (containing the desired $CF_3CH[OCH_2CF_2CFHOC_3F_6OCF_3]OH$ as a solution in excess $CF_3OC_3F_6OCFHCF_2CH_2OH$) was placed in a 600 mL Parr reaction vessel along with acetonitrile (165 g) and powdered potassium carbonate (3.1 g). The reactor was sealed, evacuated and heated to 40° C. Hexafluoropropene (31.7 g, 0.21 mole) was added in portions over one hour and the reactor then held at temperature (40° C.) overnight. The reaction mixture was worked up by pouring into water and washing the resulting lower phase three times with water followed by distillation. The main fraction had a boiling point of 190° C. The product identity was confirmed by GC-MS and H-1 NMR. The NMR data showed that the product contained about 15% olefin [—$OCF=CFCF_3$] as a cis/trans mixture. The excess alcohol was converted to $CF_3OC_3F_6OCFHCF_2CH_2OCF_2CFHCF_3$ which was removed during the distillation.

Example 8

Preparation of $CF_3CH(OCF_2CFHCF_3)OCH_2CF_2CF_2CH_2OCH(OCF_2CFHCF_3)CF_3$

Part 1: Synthesis of $CF_3CH(OH)OCH_2CF_2CF_2CH_2OCH(OH)CF_3$

This reaction was carried out in essentially the same manner as described in Example 1 using charges of sulfuric acid (175 g), $HOCH_2CF_2CF_2CH_2OH$ (19.8 g, 0.12 mol, prepared by the sodium borohydride reduction of $MeOCOCF_2CF_2CO_2Me$) and trifluoroacetaldehyde methyl hemiacetal (Alfa Aesar, 31.7 g, 90% purity, 0.22 mole). In this case the solid diol was dissolved in 100 mL of acetonitrile and this solution was placed in the receiver. The receiver had gained about 18.1 g in weight and this solution was used without purification in the next step.

Part 2: Reaction with $CF_3CF=CF_2$

The entire contents of the receiver (containing the desired bis(hemiacetal) $CF_3CH(OH)OCH_2CF_2CF_2CH_2OCH(OH)CF_3$) was placed in a 600 mL Parr reaction vessel along with additional acetonitrile (167 g total) and powdered potassium carbonate (3.0 g). The reactor was sealed, evacuated and heated to 40° C. Hexafluoropropene (51.2 g, 0.34 mole) was added in portions over one hour and the reactor then held at temperature (40° C.) overnight. The reaction mixture was worked up by pouring into water and washing the resulting lower phase three times with water followed by vacuum distillation. The main fraction had a boiling point of 102-106° C./20 mmHg. The product identity was confirmed by GC-MS and H-1 NMR. The nmr data showed that the product contained about 19.2% olefin [—OCF=CFCF_3] as a cis/trans mixture.

Various modifications and alterations of this disclosure will become apparent to those skilled in the art without departing from the scope and principles of this disclosure, and it should be understood that this disclosure is not to be unduly limited to the illustrative embodiments set forth hereinabove.

We claim:

1. A compound according to the formula:

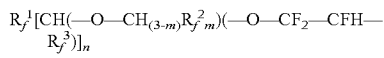  [I]

wherein n is 1 or 2,
wherein m is 1, 2 or 3,
wherein, when n is 1, $R_f^1$ is selected from the group consisting of highly fluorinated alkyl groups which are linear, branched, cyclic, or a combination thereof, which may optionally be substituted, and which may optionally contain one or more catenated heteroatoms;
wherein, when n is 2, $R_f^1$ is selected from the group consisting of highly fluorinated alkylene groups which are linear, branched, cyclic, or a combination thereof, which may optionally be substituted, and which may optionally contain one or more catenated heteroatoms;
wherein each $R_f^2$ is independently selected from the group consisting of alkyl groups which are linear, branched, cyclic, or a combination thereof, which may optionally be substituted, and which may optionally contain one or more catenated heteroatoms;
wherein at least one $R_f^2$ is highly fluorinated;
wherein each $R_f^3$ is independently selected from the group consisting of fluorine and highly fluorinated alkyl groups which are linear, branched, cyclic, or a combination thereof, which may optionally be substituted, and which may optionally contain one or more catenated heteroatoms.

2. The compound according to claim 1 wherein n is 1.
3. The compound according to claim 1 wherein m is 1.
4. The compound according to claim 1 wherein m is 2.
5. The compound according to claim 2 wherein m is 1.
6. The compound according to claim 2 wherein m is 2.
7. The compound according to claim 1 wherein $R_f^1$, $R_f^2$ and $R_f^3$ are perfluorinated.
8. The compound according to claim 1 wherein each $R_f^2$ and $R_f^3$ is independently chosen from the group consisting of perfluorinated and nearly perfluorinated C1-C4 alkyl groups which may optionally contain one or more catenated oxygen atoms.
9. The compound according to claim 2 wherein each $R_f^1$, $R_f^2$ and $R_f^3$ is independently chosen from the group consisting of perfluorinated and nearly perfluorinated C1-C4 alkyl groups which may optionally contain one or more catenated oxygen atoms.

10. The compound according to claim 1 wherein each $R_f^2$ and $R_f^3$ is independently chosen from the group consisting of perfluoromethyl and perfluoroethyl.
11. The compound according to claim 2 wherein each $R_f^1$, $R_f^2$ and $R_f^3$ is independently chosen from the group consisting of perfluoromethyl and perfluoroethyl.
12. A method of making a compound according to the formula:

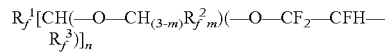  [I]

wherein n is 1 or 2,
wherein m is 1, 2 or 3,
wherein, when n is 1, $R_f^1$ is selected from the group consisting of highly fluorinated alkyl groups which are linear, branched, cyclic, or a combination thereof, which may optionally be substituted, and which may optionally contain one or more catenated heteroatoms;
wherein, when n is 2, $R_f^1$ is selected from the group consisting of highly fluorinated alkylene groups which are linear, branched, cyclic, or a combination thereof, which may optionally be substituted, and which may optionally contain one or more catenated heteroatoms;
wherein each $R_f^2$ is independently selected from the group consisting of alkyl groups which are linear, branched, cyclic, or a combination thereof, which may optionally be substituted, and which may optionally contain one or more catenated heteroatoms;
wherein at least one $R_f^2$ is highly fluorinated;
wherein each $R_f^3$ is independently selected from the group consisting of fluorine and highly fluorinated alkyl groups which are linear, branched, cyclic, or a combination thereof, which may optionally be substituted, and which may optionally contain one or more catenated heteroatoms;
the method comprising the step of:
a) reacting a compound according to the formula:

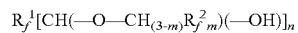  [II]

with one or more compounds according to the formula:

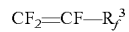  [III]

to form the compound according to the formula:

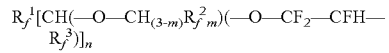  [I]

wherein n, m, $R_f^1$, $R_f^2$ and $R^3$ are as defined above.
13. The method according to claim 12 wherein step a) is performed in the presence of a catalyst.
14. The method according to claim 13 wherein the catalyst is potassium carbonate.
15. The method according to claim 12 additionally comprising the step of:
b) reacting a compound according to the formula:

  [V]

with one or more compounds according to the formula:

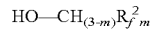  [VI]

to form the compound according to the formula:

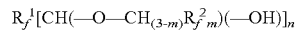  [II]

wherein n, m, $R_f^1$ and $R_f^2$ are as defined in claim 12.
16. The method according to claim 15 additionally comprising the step of:
c) reacting a compound according to the formula:

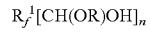  [IV]

with one or more dehydrating agents to form the compound according to the formula:

$$R_f^1[CHO]_n \quad [V]$$

wherein n and $R_f^1$ are as defined in claim 15 and R is selected from the group consisting of alkyl groups which are linear, branched, cyclic, or a combination thereof, which may optionally be substituted, and which may optionally contain one or more catenated heteroatoms.

17. The method according to claim 16 wherein one or more dehydrating agents comprises sulfuric acid.

18. The method according to claim 16 wherein step c) is performed in a first reaction chamber and the compound according to formula V formed therein is distilled from the first reaction chamber upon formation into a second reaction chamber wherein step b) is performed.

19. The method according to claim 12 wherein n is 1.

20. The method according to claim 12 wherein m is 1.

21. The method according to claim 12 wherein m is 2.

22. The method according to claim 19 wherein m is 1.

23. The method according to claim 19 wherein m is 2.

24. The method according to claim 15 wherein n is 1.

25. The method according to claim 16 wherein n is 1.

26. The method according to claim 12 wherein $R_f^1$, $R_f^2$ and $R_f^3$ are perfluorinated.

27. The method according to claim 12 wherein each $R_f^1$, $R_f^2$ and $R_f^3$ is independently chosen from the group consisting of perfluorinated and nearly perfluorinated C1-C4 alkyl groups which may optionally contain one or more catenated oxygen atoms.

28. The method according to claim 19 wherein each $R_f^1$, $R_f^2$ and $R_f^3$ is independently chosen from the group consisting of perfluorinated and nearly perfluorinated C1-C4 alkyl groups which may optionally contain one or more catenated oxygen atoms.

29. The method according to claim 12 wherein each $R_f^1$, $R_f^2$ and $R_f^3$ is independently chosen from the group consisting of perfluoromethyl and perfluoroethyl.

30. The method according to claim 15 wherein each $R_f^1$, $R_f^2$ and $R_f^3$ is independently chosen from the group consisting of perfluoromethyl and perfluoroethyl.

31. The method according to claim 16 wherein each $R_f^1$, $R_f^2$ and $R_f^3$ is independently chosen from the group consisting of perfluoromethyl and perfluoroethyl.

32. The method according to claim 19 wherein each $R_f^1$, $R_f^2$ and $R_f^3$ is independently chosen from the group consisting of perfluoromethyl and perfluoroethyl.

33. A process for removing a contaminant from an article comprising contacting said article with a composition comprising at least one compound according to claim 1.

34. A process for the extinction of fires comprising applying to a fire a composition comprising at least one compound according to claim 1.

35. A process for preparing a foamed plastic comprising vaporizing a blowing agent mixture in the presence of at least one foamable polymer or the precursors of at least one foamable polymer, said blowing agent mixture comprising at least one compound according to claim 1.

36. A process for vapor phase soldering comprising melting solder by immersing at least one component that comprises said solder in a body of fluorinated liquid vapor that comprises at least one compound according to claim 1.

37. A process for transferring heat comprising transferring heat between a heat source and a heat sink through the use of a heat transfer agent comprising at least one compound according to claim 1.

38. A process for depositing a coating on a substrate comprising applying to at least a portion of at least one surface of said substrate a composition comprising: a) a solvent composition comprising at least one compound according to claim 1; and b) at least one coating material that is soluble or dispersible in said solvent composition.

39. A process for cutting or abrasive working comprising applying a working fluid to a metal, cermet, or composite workpiece and tool, said working fluid comprising at least one compound according to claim 1 and at least one lubricious additive.

40. A polymerization process comprising polymerizing at least one monomer in the presence of at least one polymerization initiator and at least one compound according to claim 1.

41. A mixture of diastereomers of the compound according claim 1 which exhibit the same enantiomeric form at each carbon marked with an asterisk in formula I':

$$R_f^1[C^*H(-O-CH_{(3-m)}R_f^2{}_m)(-O-CF_2-C^*FH-R_f^3)]_n \quad [I']$$

42. A mixture of diastereomers of the compound according claim 1 which exhibit (S)-enantiomeric form at at least one carbon marked with an asterisk in formula I' and exhibit (R)-enantiomeric form at at least one carbon marked with an asterisk in formula I':

$$R_f^1[C^*H(-O-CH_{(3-m)}R_f^2m)(-O-CF_2-C^*FH-R_f^3)]_n \quad [I]$$

43. A compound according claim 1 which is a single enantiomer.

44. A compound according claim 1 which is a (+)-enantiomer.

45. A compound according claim 1 which is a (−)-enantiomer.

* * * * *

UNITED STATES PATENT AND TRADEMARK OFFICE
CERTIFICATE OF CORRECTION

| | |
|---|---|
| PATENT NO. | : 8,071,816 B2 |
| APPLICATION NO. | : 12/164369 |
| DATED | : December 6, 2011 |
| INVENTOR(S) | : Richard Mark Flynn et al. |

It is certified that error appears in the above-identified patent and that said Letters Patent is hereby corrected as shown below:

Title Page

Item [56], References Cited, OTHER PUBLICATIONS, delete "Rhdroftuoroethers" and insert -- Hydrofluoroethers -- therefor.

delete "Journal of Fiuorine" and insert -- Journal of Fluorine -- therefor.

Column 1

Line 47, delete "$R_f^3]_n$     [I]" and insert -- $R_f^3)]_n$     [I'] -- therefor.

Column 2

Line 66, delete "$R_{f\,m)}^2$" and insert -- $R_{f\,m}^2)$ -- therefor.

Line 67, delete "$R_f^3]_n$" and insert -- $R_f^3)]_n$ -- therefor.

Column 11

Line 30, delete "H-1and" and insert -- H-1 and -- therefor.

Line 44, delete "D1" and insert -- DI -- therefor.

Line 52, delete "D1" and insert -- DI -- therefor.

Column 18

Claim 41, Line 32, delete "according" and insert -- according to -- therefor.

Claim 41, Line 36, after $R_f^3)]_n$ insert -- . -- therefor.

Claim 42, Line 37, delete "according" and insert -- according to -- therefor.

Claim 42, Line 42, delete "$R_{f\,m)}^2$" and insert -- $R_{f\,m}^2)$ -- therefor.

Signed and Sealed this
Fifteenth Day of May, 2012

David J. Kappos
*Director of the United States Patent and Trademark Office*

CERTIFICATE OF CORRECTION (continued)
U.S. Pat. No. 8,071,816 B2

Claim 42, Line 43, delete "[I]" and insert -- [I'] -- therefor.

Claim 42, Line 43, after $R_f^3)]_n$ insert -- . -- therefor.

Claim 43, Line 45, delete "according" and insert -- according to -- therefor.

Claim 44, Line 47, delete "according" and insert -- according to -- therefor.

Claim 45, Line 49, delete "according" and insert -- according to -- therefor.

UNITED STATES PATENT AND TRADEMARK OFFICE
CERTIFICATE OF CORRECTION

PATENT NO. : 8,071,816 B2
APPLICATION NO. : 12/164369
DATED : December 6, 2011
INVENTOR(S) : Richard Mark Flynn et al.

It is certified that error appears in the above-identified patent and that said Letters Patent is hereby corrected as shown below:

In the Specifications:

Column 4

Line 10, delete "$R_f^3]_n$" and insert -- $R_f^3)]_n$ -- therefor.

Column 14

Line 11 – 12, delete "13020 C." and insert -- 130°C. -- therefor.

Signed and Sealed this
Ninth Day of July, 2013

Teresa Stanek Rea
*Acting Director of the United States Patent and Trademark Office*